United States Patent
Cockerham et al.

(10) Patent No.: US 11,495,349 B2
(45) Date of Patent: Nov. 8, 2022

(54) PERFORMANCE VISUALIZATION METHODS AND DIAGNOSTIC LABORATORY SYSTEMS INCLUDING SAME

(71) Applicant: Siemens Healthcare Diagnostics Inc., Tarrytown, NY (US)

(72) Inventors: Gregory Cockerham, Hight Point, NC (US); Michael Heydlauf, Cary, NC (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 17/755,811

(22) PCT Filed: Jan. 15, 2021

(86) PCT No.: PCT/US2021/070045
§ 371 (c)(1),
(2) Date: May 9, 2022

(87) PCT Pub. No.: WO2021/159132
PCT Pub. Date: Aug. 12, 2021

(65) Prior Publication Data
US 2022/0293255 A1 Sep. 15, 2022

Related U.S. Application Data

(60) Provisional application No. 62/971,290, filed on Feb. 7, 2020.

(51) Int. Cl.
*G16H 40/20* (2018.01)
*G06T 11/00* (2006.01)

(52) U.S. Cl.
CPC .......... *G16H 40/20* (2018.01); *G06T 11/001* (2013.01)

(58) Field of Classification Search
CPC ............................. G16H 40/20; G06T 11/001
See application file for complete search history.

(56) References Cited

U.S. PATENT DOCUMENTS 8,069,239 B2   11/2011   Trochman
8,648,910 B2    2/2014   Heydlauf
(Continued)

FOREIGN PATENT DOCUMENTS

WO       2010099170       9/2010
WO    WO-2010099170 A1 *  9/2010   ............ G06F 11/008

OTHER PUBLICATIONS

Vassy, Zsolt; Kosa, Istvan; Vassanyi, Istvan. "Correlation Clustering of Stable Angina Clinical Care Patterns for 506 Thousand Patients." Journal of Healthcare Engineering. 2017 : NA. Hindawi Limited. (2017) (Year: 2017).*

(Continued)

*Primary Examiner* — Linh Giang Le

(57) ABSTRACT

Methods of visualizing performance of a diagnostic laboratory system are provided. The methods include displaying on a display, an image representing a layout of a plurality of laboratory analyzers included within the diagnostic laboratory system, and overlaying the image with a dynamically-changeable color overlay that indicates a performance for the plurality of laboratory analyzers over a period of time via using changeable colors. Systems including color-changeable overlays are provided as are other aspects.

4 Claims, 8 Drawing Sheets

(56) References Cited

U.S. PATENT DOCUMENTS

| | | |
|---|---|---|
| 10,360,238 B1 | 7/2019 | O'Brien et al. |
| 2009/0222746 A1* | 9/2009 | Chirica .................. G06Q 10/06 715/802 |
| 2011/0040593 A1 | 2/2011 | Depreter |
| 2013/0207812 A1 | 8/2013 | Heydlauf |
| 2016/0260215 A1* | 9/2016 | Burg ..................... G06T 7/0014 |
| 2017/0220775 A1 | 8/2017 | de la Torre-Bueno |

OTHER PUBLICATIONS

International Search Report for PCT/US21/70045 dated Apr. 28, 2021.

* cited by examiner

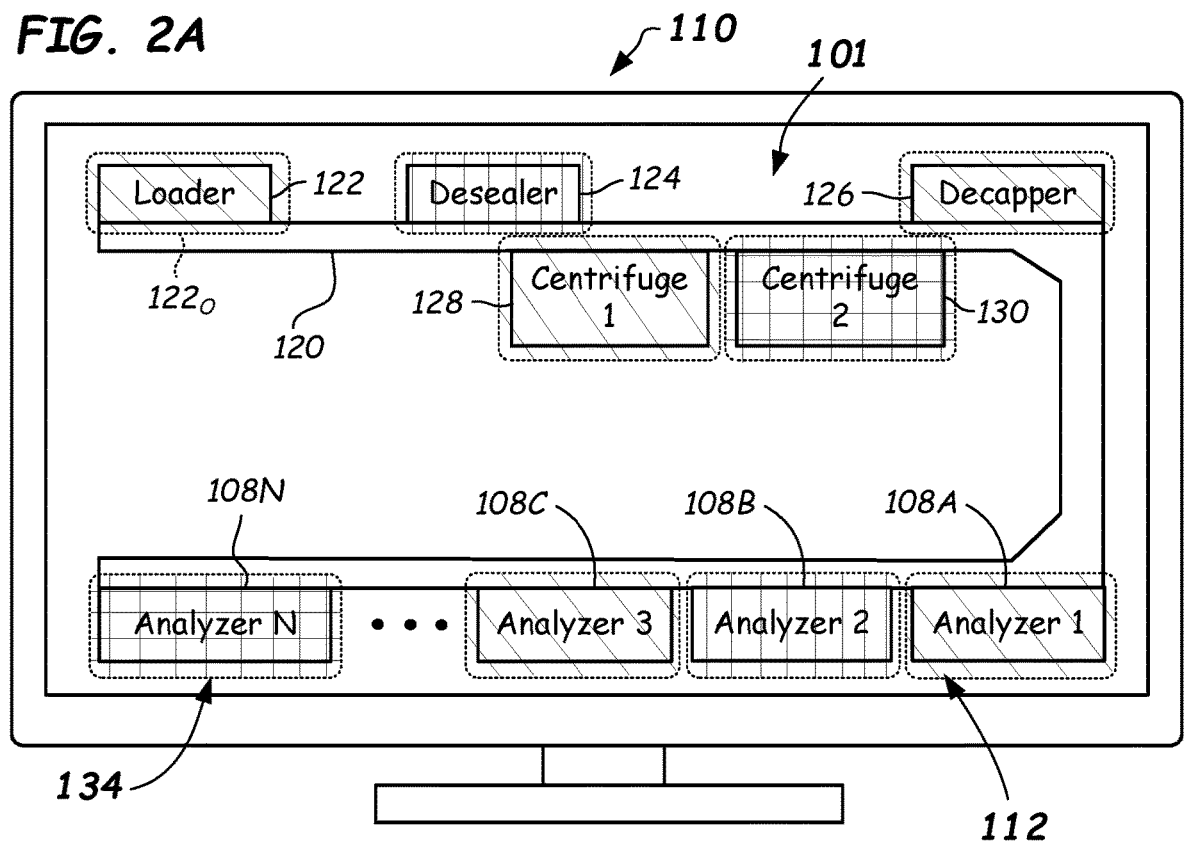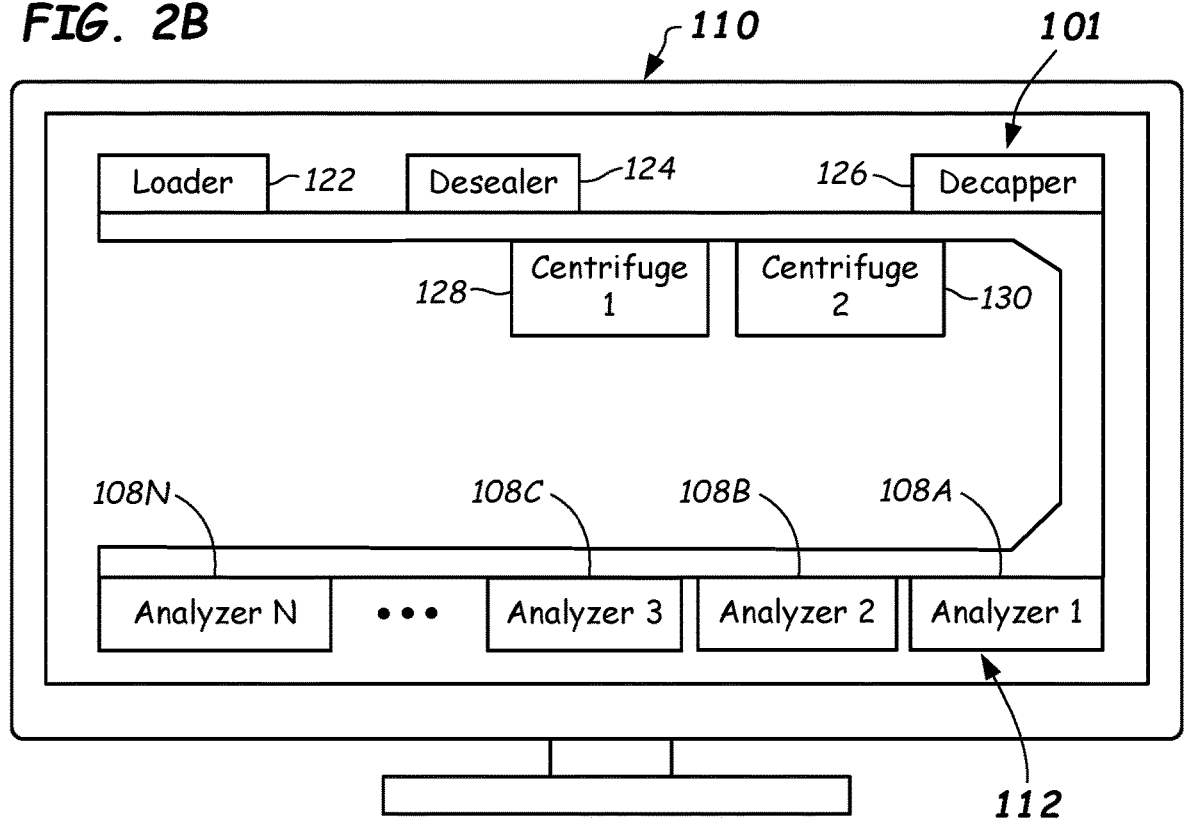

80% Transparent

55% Transparent

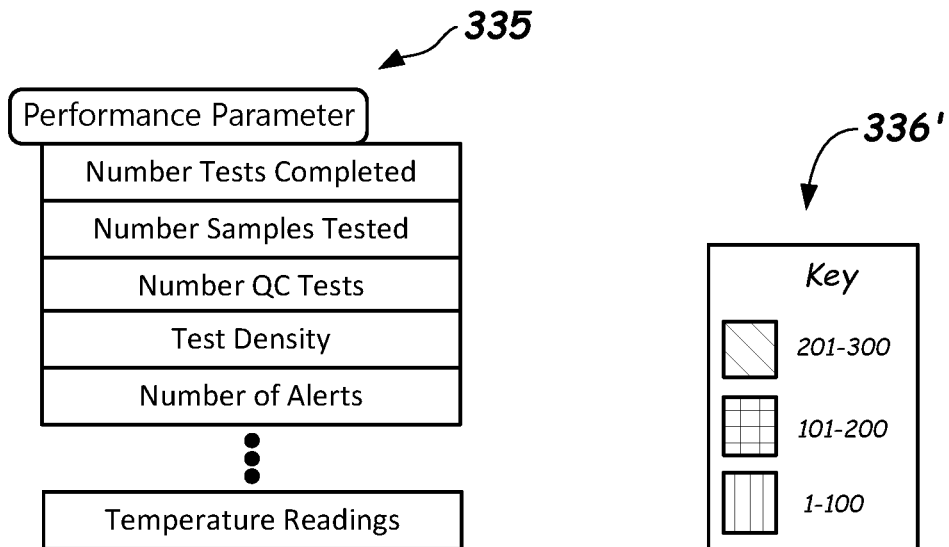
FIG. 3J
FIG. 3L
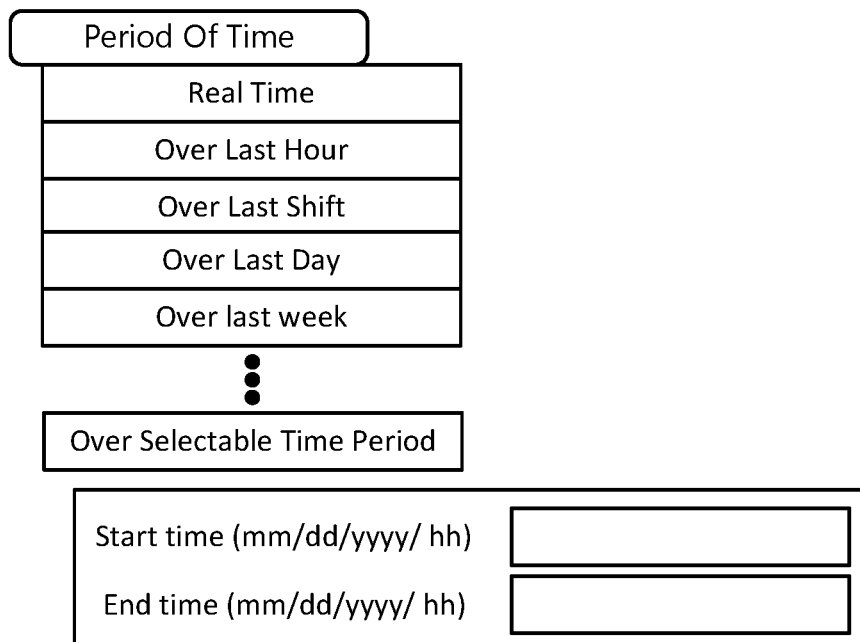
FIG. 3K

PERFORMANCE VISUALIZATION METHODS AND DIAGNOSTIC LABORATORY SYSTEMS INCLUDING SAME

FIELD

This disclosure relates to systems and methods that provide insight into the performance of a diagnostic laboratory.

BACKGROUND

Centralization and consolidation of multiple small-scale diagnostic laboratories into larger-scale diagnostic laboratories for the analysis of bio-fluid samples (e.g., blood, blood plasma, blood serum, urine, cerebrospinal fluid, etc.) has been a trend in recent years. This trend is driven primarily by reductions in reimbursements by health insurers for the most frequently-ordered laboratory tests. In view of the small profit margins, continued operation by many small-scale diagnostic laboratories may be difficult, especially if reimbursement rates continue to drop. Thus, centralization and consolidation of small-scale diagnostic laboratories into larger-scale diagnostic laboratories is likely to continue.

In operation, large-scale diagnostic laboratories may process millions of bio-fluid samples each year across a large number of laboratory analyzers (e.g., 20+). In addition to the laboratory analyzers, there may be ancillary test processing equipment such as one or more sample container loaders, desealers, centrifuges, decappers, and the like that preprocess the samples and/or containers before they arrive at an analyzer for testing of the samples. In some embodiments, the large number of laboratory analyzers may be interconnected via an automated track. Many of the laboratory analyzers may have similar or overlapping capabilities in that they may run a large number of the same or differing tests thereon. The operations of such large-scale diagnostic laboratories undergo continuous monitoring, evaluation, and intervention/manipulation by human operators. This may be done to ensure that test results are accurate, to allow for STAT tests to be incorporated and maintenance to be conducted, for example.

SUMMARY

According to a first aspect, a method of visualizing performance of a diagnostic laboratory system is provided. The method includes displaying on a display, an image representing a layout of a plurality of laboratory analyzers included within the diagnostic laboratory system, and overlaying the image with a dynamically-changeable color overlay that indicates a performance for the plurality of laboratory analyzers over a period of time. The period of time may be in real time, a running average, or a selectable time period.

In a further aspect, a diagnostic laboratory system is provided. The diagnostic laboratory system includes a lab server having a processor and memory; and a plurality of laboratory analyzers configured to communicate with the lab server, each of the plurality of laboratory analyzers further configured to perform tests on biological samples. The lab server further comprises a display configured to display an image representing a layout of a plurality of laboratory analyzers; a performance database stored in the memory configured to receive performance data regarding the plurality of laboratory analyzers; and a color overlay module comprising computer executable instructions configured to generate a dynamically-changeable color overlay to be displayed relative to the layout whose colors are changeable based on the performance data received in the performance database regarding the plurality of laboratory analyzers.

According to another aspect, a non-transitory, computer-readable storage medium is provided. The non-transitory computer readable storage medium includes a color overlay module having computer executable instructions configured to cause a lab server to: receive performance data for a diagnostic laboratory system comprising a plurality of laboratory analyzers; store the performance data in a performance database; generate image data of an image of a layout of the plurality of laboratory analyzers; generate a dynamically-changeable color overlay; and cause the display of the dynamically-changeable color overlay relative to image of the layout of the plurality of laboratory analyzers based on the performance data, wherein respective colors of the dynamically-changeable color overlay are changeable in response to a change in performance.

Still other aspects, features, and advantages of this disclosure may be readily apparent from the following description and illustration of a number of example embodiments, including the best mode contemplated for carrying out the disclosure. This disclosure may also be capable of other and different embodiments, and its several details may be modified in various respects, all without departing from the scope of the invention. This disclosure is intended to cover all modifications, equivalents, and alternatives falling within the scope of the claims and their equivalents.

BRIEF DESCRIPTION OF THE DRAWINGS

The drawings, described below, are for illustrative purposes and are not necessarily drawn to scale. Accordingly, the drawings and descriptions are to be regarded as illustrative in nature, and not as restrictive. The drawings are not intended to limit the scope of the invention in any way.

FIG. 2A illustrates a schematic diagram of a display configured to display images of a layout of laboratory analyzers and possibly ancillary test processing equipment according to one or more embodiments, wherein the display includes a dynamically-changeable color overlay that provides colorization that denotes a performance of the plurality of laboratory analyzers and possibly also of the ancillary test processing equipment over a time period.

FIG. 2B illustrates a schematic diagram of a display that is displaying an image of the layout of the laboratory analyzers and possibly ancillary test processing equipment located within the diagnostic laboratory as a two-dimensional (2D) image, with the dynamically-changeable color overlay removed for illustration purposes, according to one or more embodiments.

FIG. 3J illustrates a diagram of a drop down menu illustrating selectable performance parameter options to display according to one or more embodiments.

FIG. 3K illustrates a diagram of a drop down menu illustrating selectable options for the period of time over which a performance parameter is to be displayed according to one or more embodiments.

FIG. 3L illustrates a diagram of an example key illustrating display colors for the individual color overlays for a pre-selected or user selected performance parameter having a count according to one or more embodiments.

DETAILED DESCRIPTION

Figure 1:
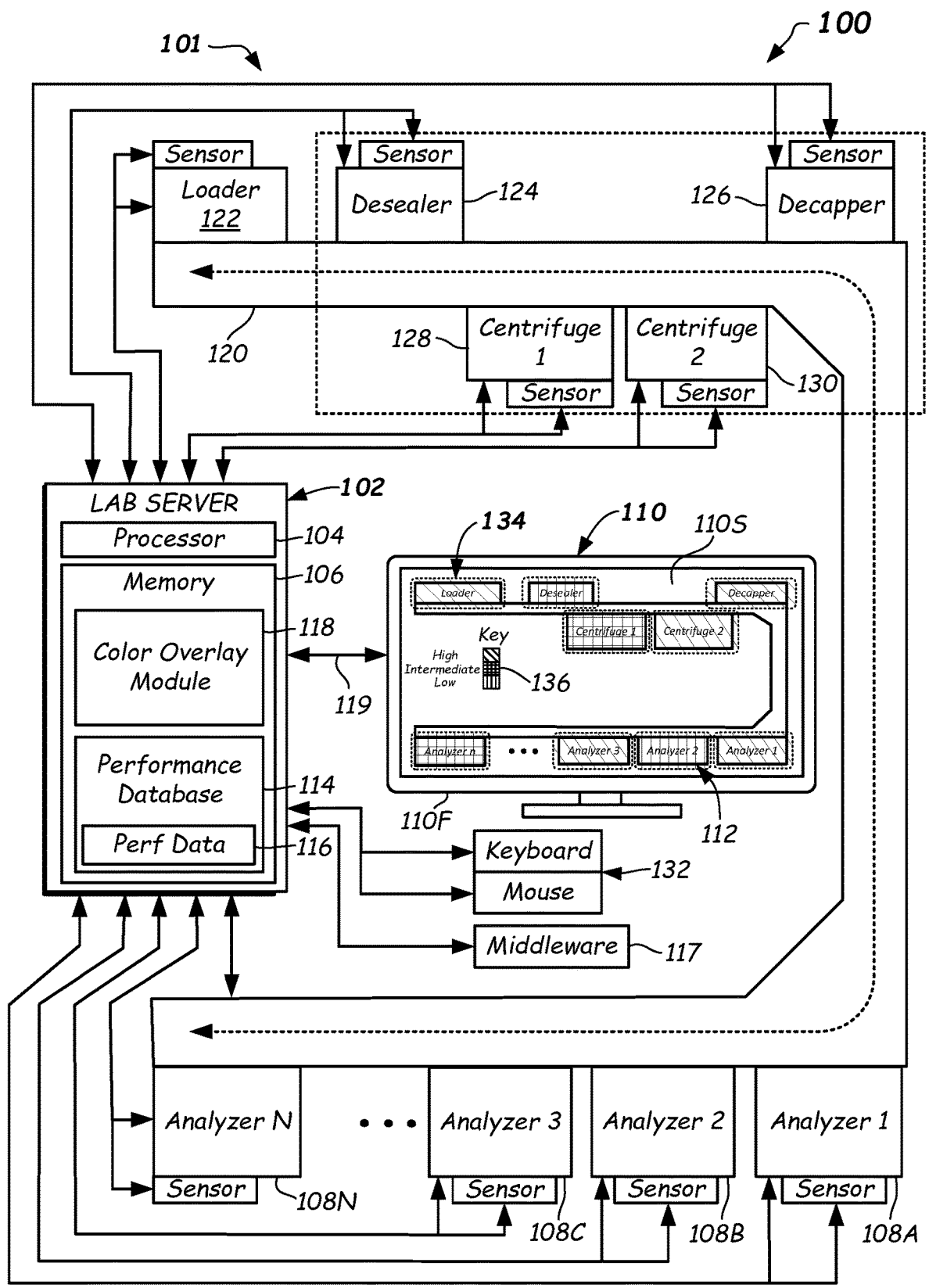
FIG. 1 illustrates a schematic block diagram of a diagnostic laboratory system including a dynamically-changeable color overlay to provide performance visualization over a period of time according to one or more embodiments.

Compared to small-scale diagnostic laboratories where only a limited number of laboratory analyzers are used, opportunities to increase efficiency arise with the use of multiple laboratory analyzers that have the same and/or overlapping test (e.g., assay and/or clinical chemistry) menus. In particular, when facilitating maintenance, shut down due to unforeseen circumstances, addition of large numbers of STAT tests, and the like, it may be difficult to readily understand how such changes can affect the overall throughput of the laboratory over a particular period of time. In particular, there is an unmet need to improve operational efficiency of large-scale diagnostic laboratories by providing improved and rapid understanding and visualization of how any such changes affect performance across the multiple laboratory analyzers and possibly ancillary test processing equipment.

In these cases of workload disruptions or changes, workload may be shifted to other analyzers and/or ancillary test processing equipment within the diagnostic laboratory. In such instances, it was recognized by the inventors that having the ability to rapidly (within minutes) understand and visualize how any such changes made have affected the overall performance of the analyzers and/or ancillary test processing equipment within the diagnostic laboratory is helpful. For example, performance parameters such as workflow and workflow balance within the analyzers and/or ancillary test processing equipment within the diagnostic laboratory may be rapidly visualized.

Therefore, embodiments of the systems and methods herein may advantageously provide improved visualization of any measurable performance parameter of the diagnostic laboratory and, in particular, can provide improved visualization of workload balancing thereof, for example. Such rapid visualization can help increase throughput, while responding to STAT requests and accommodating unforeseen analyzer and equipment maintenance and downtime due to unforeseen situations, malfunctions, and the like. Providing improved ability to visualize and further respond and provide workload balancing across each laboratory analyzer as well as across the pieces of ancillary test processing equipment can improve overall average time per test and can have other tangible benefits.

Thus, the ability to rapidly visualize and manage the use of laboratory analyzers and/or ancillary test processing equipment for improved workflow balance or other performance parameter, for example, can lead to lower overall system costs and improved system flexibility. Thus, in accordance with this disclosure, embodiments provide improved performance parameter visualization of the diagnostic laboratory system. The performance parameter visualization may be provided over any desired period of time, such as substantially instantaneously (i.e., in real time), over a few minutes, or over any suitable longer and selectable period of time in the past. The displayed updates can be based on a running average over a period of time, such as over a number of minutes or hours.

The performance parameter visualization may include visualization of any performance parameter that is an operational or other changeable parameter capable of being counted or measured in the diagnostic laboratory. The performance parameter can include, but is not limited to, any of the following over a period of time, for example:

Tests completed by a particular laboratory analyzer.
Samples tested by a particular laboratory analyzer.
Quality control tests conducted by a particular laboratory analyzer.
Alerts on a particular laboratory analyzer or particular piece of ancillary test processing equipment.
Operator interactions on a particular laboratory analyzer or particular piece of ancillary test processing equipment.
Log messages on a particular laboratory analyzer or particular piece of ancillary test processing equipment.
Down time (or up time) on a particular laboratory analyzer or particular piece of ancillary test processing equipment.
Maintenance time on a particular laboratory analyzer or particular piece of ancillary test processing equipment.
Amount of an inventory item on a particular laboratory analyzer.
Amount of waste item on a particular laboratory analyzer.
Time for and/or number of procedures completed by a particular piece of ancillary test processing equipment.
Maintenance completed for a particular piece of ancillary test processing equipment.
Temperature of particular laboratory analyzer and/or piece of ancillary test processing equipment.
Voltage or current of particular laboratory analyzer and/or piece of ancillary test processing equipment.
Vibration of a particular laboratory analyzer and/or piece of ancillary test processing equipment.

The systems and methods providing such performance parameter visualization according to embodiments may be provided by utilizing color as a means to visualize any performance parameter. The color may be used as part of a dynamically-changeable color overlay of a display in some embodiments. In particular, colors can be assigned to the dynamically-changeable color overlay, and individual color overlays of the dynamically-changeable color overlay can be associated with a particular analyzer and/or piece of ancillary process equipment. For example, the individual color overlays can overlie a graphical figure of the analyzers and/or pieces of ancillary test processing equipment that is displayed on the display (e.g., display monitor, display screen, projected display, or the like). Thus, a particular color can be associated with an extent of any performance parameter for individual ones of the analyzers and/or individual pieces of ancillary test processing equipment. Individual color overlays are color changeable to signify a change in a performance parameter.

An overlay color (e.g., green, yellow, red, etc.) may be assigned to each individual overlay associated with a laboratory analyzer and/or piece of ancillary test processing equipment and that overlay color can be tied to a measured or counted performance parameter by accessing stored performance data. The performance data can be received at a lab server from each of the laboratory analyzers and/or each of the pieces of ancillary processing equipment, for example. Optionally, the performance data may be received from another software program or another database, for example. Performance data may be provided by any suitable measurement technology, such as an output signal from a sensor or sensors or other suitable counting mechanism of the laboratory analyzers and/or each piece of ancillary processing equipment that can provide performance data.

Performance data can be any data representative of a performance parameter of a particular laboratory analyzer and/or piece of ancillary test processing equipment. For example, performance data can comprise one or more or any combination of the following:

- Count of a number of tests completed by a particular laboratory analyzer over a period of time.
- Count of a number of samples tested by a particular laboratory analyzer over a period of time.
- Count of a number of quality control tests completed by a particular laboratory analyzer over a period of time.
- Count of a number of alerts on a particular laboratory analyzer and/or particular piece of ancillary test processing equipment over a period of time
- Count of a number of operator interactions on a particular laboratory analyzer and/or particular piece of ancillary test processing equipment over a period of time.
- Count of a number of log messages on a particular laboratory analyzer and/or particular piece of ancillary test processing equipment over a period of time.
- Count of an amount of down time (and/or up time) on a particular laboratory analyzer and/or particular piece of ancillary test processing equipment over a period of time.
- Count of an amount of maintenance time on a particular laboratory analyzer and/or particular piece of ancillary test processing equipment over a period of time.
- Whether maintenance has been completed for a particular laboratory analyzer and/or particular piece of ancillary test processing equipment over a period of time.
- Count of an amount of an inventory item (e.g., reagent, water, and/or substrate (cuvettes, 96 well plates, etc.)) on a particular laboratory analyzer over a period of time.
- Count (weight or other measure) of an amount of a waste item (e.g., a waste item such as waste water weight, waste bin weight, and the like) on a particular laboratory analyzer over a period of time.
- Count of a number of tests and/or procedures completed by a particular piece of ancillary test processing equipment over a period of time.
- Temperature readings of some portion of a particular laboratory analyzer and/or piece of ancillary test processing equipment over a period of time.
- Voltage or current sensor readings of particular laboratory analyzer and/or piece of ancillary test processing equipment.
- Vibration sensor readings of particular laboratory analyzer and/or piece of ancillary test processing equipment.

Any suitable colorization scheme may be used in the dynamically-changeable color overlay. For example, a heat map overlay colorization may be used. Heat map overlay colorization may include colors that are changeable based on an extent of performance (e.g., of a selected performance parameter) such as at least green, yellow, and red. Green can denote, for example, optimal, high, or fast; yellow can denote less than optimal, medium, or moderate; and red can denote non-optimal, low, or stopped, respectively. Optionally, the changeable colors can denote a level of fullness, such as green—full, yellow—about half full, and red—about empty or in need of filling. Other colors or shades of color may be used to visualize one or more types of performance parameters over the period of time. For example, dark green may be used for fully optimized and lime green for moderately optimized. The dynamically-changeable color overlay may include individual color overlays that correspond to each of the respective laboratory analyzers and their colors may each be changeable to reflect an existing performance over the period of time (e.g., instantaneous or real time or over a preselected or user-selectable period of time.

Further details of inventive laboratory analyzer system and methods will be described with reference to FIGS. 1-5 herein.

FIG. 1 illustrates a laboratory analyzer system 100 according to embodiments of the disclosure. Laboratory analyzer system 100 may automatically process large numbers of biological samples with minimal human intervention, except possibly for the introduction of STAT tests, maintenance, and service for breakdowns and work stoppages. Laboratory analyzer system 100 may include a lab server 102 and a plurality of laboratory analyzers (represented by laboratory analyzers 108A, 108B, and 108C-108N) in communication therewith. Laboratory analyzer system 100 may further include one or more pieces of ancillary test processing equipment 101, such as, for example, a loader 122, desealer 124, centrifuge 128, 130, and decapper 124. Other ancillary test processing equipment 101 may be included, such as a quality check station, to check the specimen for one or more characteristics, such as a volume of serum or plasma, the presence of an interferent such as Hemolysis, Icterus, Lipemia (HIL) in the serum or plasma, or the presence of another interferent such as a blood clot, bubble, or foam therein. An ancillary test processing equipment 101 is any piece of equipment that is ancillary to the laboratory analyzers 108A-108N in that the piece of ancillary test processing equipment 101 performs a process or test on the sample or on the sample container prior to analysis is of the sample by one or more of the laboratory analyzers 108A, 108B, and 108C-108N).

Communication between the laboratory analyzers 108A, 108B, 108C-108N and the ancillary test processing equipment 101 can be accomplished by any suitable means, such as digital communication on a suitable computer network, such as a local area network (LAN), a wireless local area network (WLAN), power line communication (PLC), and the like, for example. Other suitable forms of digital or electronic communication may be used.

An automated track 120 may be configured to transport sample containers (not shown) to and from the loader 122 as well as to and from some of the ancillary test processing equipment 101 and to and from each of the laboratory analyzers 108A-108N within laboratory analyzer system 100. Sample containers may each be provided with one or more labels that may include identification information thereon, such as, a time and/or date stamp, requested test(s), patient identification, and the like. The label(s) may include, e.g., a barcode and/or have alphanumeric information printed thereon. The identification information may be machine readable at various locations about laboratory analyzer system 100. Sample containers may include caps and may be sealed in some instances. Automated track 120 may be a railed track (e.g., a mono rail or a multiple rail), a collection of conveyor belts, conveyor chains, moveable platforms, or any other suitable type of conveyance mechanism. Automated track 120 may be circular or other suitable shapes and may be a closed track (e.g., an endless track), and may have paths as offshoots from a main track in some embodiments.

Lab server 102 may be in digital communication with a display 110 that is configured to display performance data about the operation and/or performance of the various laboratory analyzers 108A-108N and/or one or more pieces of ancillary test processing equipment 101 of the laboratory analyzer system 100. The lab server 102 may optionally control the operation of some of the automated track 120, ancillary test processing equipment 101, and may possibly control the operation of some or all aspects of one or more of the laboratory analyzers 108A-108N. However, generally, each laboratory analyzers 108A-108N includes a workstation or controller configured to control operation thereof for carrying out various types of testing on biological samples thereon. Laboratory analyzers 108A-108N are configured to perform one or more types of diagnostic tests and/or analyses on biological samples delivered thereto by the automated track 120.

The diagnostic testing carried out on the analyzers 108A-108N can include, but is not limited to, immunoassay testing (e.g., chemiluminescent immunoassays (CLIA), radioimmunoassays (RIA), counting immunoassays (CIA), fluoroimmunoassays (FIA), and enzyme immunoassays (EIA and including enzyme linked immunosorbent assays (ELISA)), to target a specific target biomolecule, clinical chemistry analyzers to measure concentrations of substances (e.g., glucose, Hemoglobin A1C, lipids (fats), triglycerides, blood gases (e.g., carbon dioxide, etc.), enzymes, electrolytes (e.g., sodium, potassium, chloride, and bicarbonate), lipase, bilirubin, creatinine, blood urea nitrogen (BUN), hormones (e.g., thyroid stimulating hormone), hepatitis, minerals (e.g., iron. calcium, magnesium, etc.), proteins, and other metabolic products and the like) in biological samples. Other testing may be performed on the biological samples by the laboratory analyzers 108A-108N of laboratory analyzer system 100. Biological samples can include whole blood, serum, plasma, urine, cerebral-spinal fluid, interstitial fluid, saliva, feces, and the like.

In some embodiments, many of the laboratory analyzers 108A-108N of the laboratory analyzer system 100 may be capable of performing the same menu of tests, while others of the laboratory analyzers 108A-108N may be capable of performing only a limited number of tests or only certain individual tests.

Lab server 102 may include any suitable processor 104, e.g., a microprocessor-based, central processing unit (CPU) or other suitable digital processor configured to execute programming instructions, a suitable memory 106 such as a combination of random access memory (RAM) and read-only memory (ROM), software and/or firmware, and other suitable electronics and hardware configured for communication with and control of the operation of laboratory analyzer system 100 as well as for displaying on the display 110 of various types of performance data for the laboratory analyzers 108A-108N and/or one or more pieces of ancillary test processing equipment 101.

In some embodiments, laboratory analyzer system 100 may have 20 or more, 30 or more, 40 or more, 50 or more, 60 or more, 70 or more, 80 or more, 90 or more, or even 100 or more laboratory analyzers 108A-108N (where N can be any integer). Each of the laboratory analyzers 108A-108N can consume inventory and some of the performance data may be the amount of inventory present on one or more of the laboratory analyzers 108A-108N (e.g., a numerical count of an amount of reagent (e.g., volume), number of substrates, number of containers, and the like). Numerical counts, weights, distances, heights, vibration, or other performance measures of any performance parameter may be stored and used for display. For example, numerical counts, weights, distances, heights, or other performance measures of an extent of inventory can be digitally communicated to the lab server 102 through a data router and stored as performance data 116 in a performance database 114. Other performance data 116 may be received from sensors on the laboratory analyzers 108A-108N and/or pieces of ancillary test processing equipment 101. Sensors may be position or distance sensors, temperature sensors, load sensors, vibration sensors, and the like. Performance data 116 may be received directly from the sensors or workstations of the laboratory analyzers 108A-108N and/or pieces of ancillary test processing equipment 101 or indirectly from other sources, such as from middleware 117, which may receive the performance data from the sensors or workstations of the laboratory analyzers 108A-108N and/or pieces of ancillary test processing equipment 101. Middleware 117 may be a software program that assist with inventory and load control of the laboratory analyzers 108A-108N and/or pieces of ancillary test processing equipment 101.

Again referring to FIG. 1, display 110 may be communicatively coupled to the lab server 102, such as by a communication cable and suitable graphics card denoted by arrow 119, or optionally wirelessly such as through a WIFI connection or through a digital cellular network connection. Display 110, may be as shown, any suitable display screen including a display frame 110F and a display screen 110S. Display screen may comprise a cathode ray tube (CRT) display, a light-emitting diode (LED) display, an electroluminescent display (ELD), electronic paper or E ink, a plasma display panel (PDP), a liquid crystal display (LCD), an organic light-emitting diode (OLED) display, a digital light processing (DLP) display, and the like, that is configured to display a visual image of the layout. Display 110 can be a touch screen. Display can be a hand-held device, such as a cell phone or a tablet. Optionally, display 110 may be a surface that receives an image projected by an image projector in digital communication with the lab server 102.

User interface 132 may include a user input device (e.g., keyboard, touch screen, etc.) for entering (e.g., data, requests for status, operational and control commands, etc.) to the lab server 102. User interface 132 may also include a mouse configured to select from various dropdown or user-selectable options. For example, user interface 132 may enable selection of user-selectable options such as between the various performance data options to display on the display 110 for the plurality of laboratory analyzers 108A-108N and/or one or more pieces of ancillary test processing equipment 101. In some embodiments, the period of time may be provided in real time to provide an instantaneous readout and indication of performance. Further, the period of time over which to display the selected performance data may be pre-selected or optionally user selectable in some embodiments.

Real time may be considered a count or measurement over a relatively short period of time or instantaneously. In some embodiments, the display of the performance parameter can be a moving average. The display of performance data as a dynamically-changeable overlay 134 on the display 110 may be based on a running average over a relatively-short period of time, such as a minute or less, in some embodiments. Thus, a displayed running average may be an average of multiple data points over the last several (e.g., three minutes or less). However the period of time over which the performance data is displayed can be any other suitable period of time, such as an hour, a shift, a day, a week, and the like. The period of time over which the performance data is displayed can be any selected period of time, such as in a user-selectable option where the user specifies a start and end date and/or time. The particular performance data to be displayed can be selected by the user (user selectable) such as by a drag down menu, touch screen, or other suitable selection method.

Figure 2C:
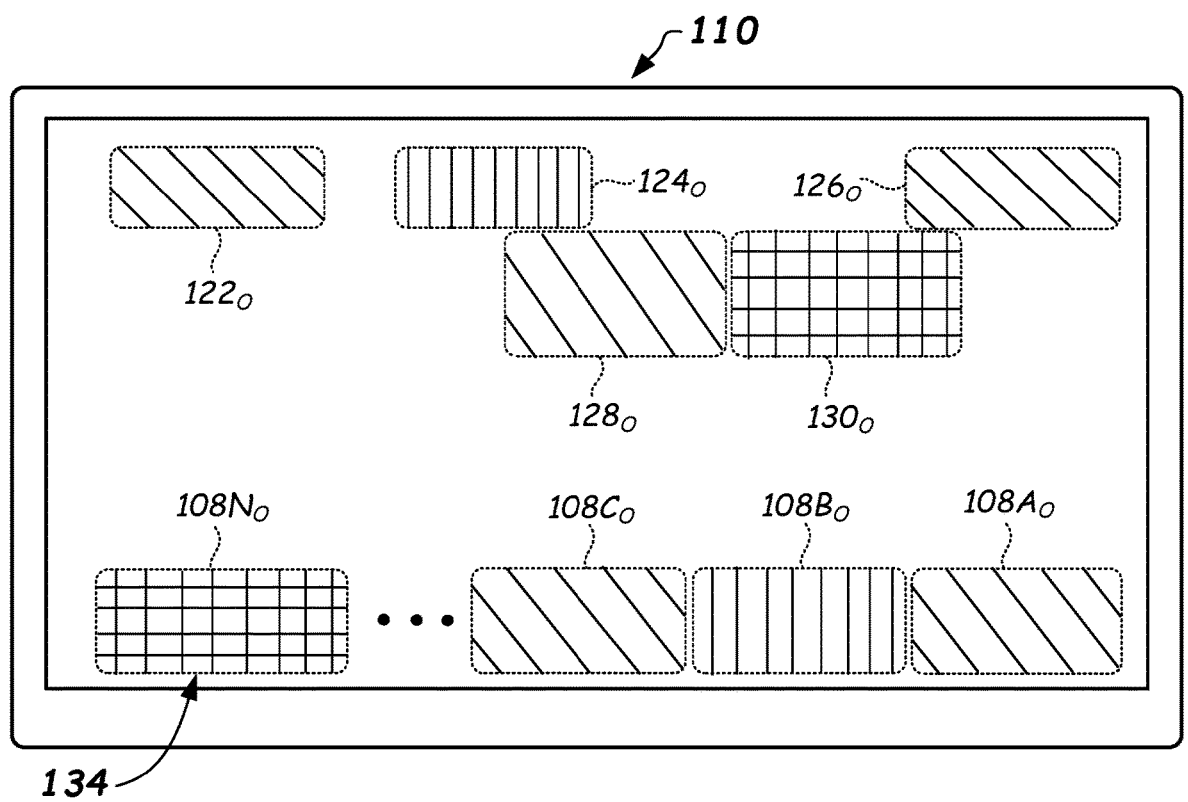
FIG. 2C illustrates a schematic diagram of a display that is displaying an image of the dynamically-changeable color overlay, with the image of the layout of laboratory analyzers and possibly ancillary test processing equipment being removed for illustration purposes, according to one or more embodiments.

As shown in FIGS. 2A-2C, the display 110 is configured to display a representative image 112 of a layout of the diagnostic laboratory system 100. For example, the image 112 of the layout may be a two-dimensional (2D) image (see FIGS. 2A and 2B) or three-dimensional (3D) image (see FIG. 3A) showing, on the display 110 (e.g., on the display screen 110S or other display), the relative or approximate locations of the laboratory analyzers 108A-108N within the diagnostic laboratory system 100. The display 110 may also be configured to display an image of a relative or approximate location of the one or more pieces of ancillary test processing equipment 101 in the diagnostic laboratory system 100. For example, the pieces of ancillary test processing equipment 101 can be a loader 122, a desealer 124, a decapper 126, and/or one or more centrifuges 128, 130, for example. The ancillary test processing equipment 101 can be arranged around an automated track 120. In some embodiments, even the automated track 120 can be considered a piece of ancillary test processing equipment 101. Other or different types of ancillary test processing equipment 101 can be displayed as part of the image 112.

Overlaying the image 112 of the layout of the laboratory analyzers 108A-108N and possibly including the layout of one or more pieces of ancillary test processing equipment 101 in the diagnostic laboratory system 100 is a dynamically-changeable color overlay 134 on the display 110. One possible embodiment of the dynamically-changeable overlay 134 is best shown in isolation, for illustrative purposes, on the display 110 shown in FIG. 2C. The dynamically-changeable color overlay 134 is made up of a plurality of individual color overlays (each designated with the subscript O). For illustration purposes, the individual color overlays are shown with dotted borders. However, no such dotted line border, or any line border, is needed to be provided on the individual color overlays on the display 110, i.e., they may not include a border line.

The plurality of individual color overlays as shown (e.g., color overlays $108A_o$-$108NO$, $122_o$, $124_o$, $126_o$, $128_o$, $130_o$) are positioned on the display 110 so that they are associated with (e.g., at least partially overlap with) the respective representative geometric figures in the image 112 representing the laboratory analyzers 108A-108N, and if included, the one or more pieces of ancillary test processing equipment 101 in the diagnostic laboratory system 100. Overlay as used herein means laying on, above, below, surrounding, or immediately proximate the location of the representative geometric figures. A circumscribed area of the individual color overlays may be immediately proximate with, coincide with, partially coincide with, or surround the area of the geometric figures representing the laboratory analyzers 108A-108N (and one or more pieces of ancillary test processing equipment 101, if included).

Various embodiments showing different types of individual color overlays including various overlap and patterns are shown in FIGS. 3B-3I. In each of the embodiments shown, a portion of the image 112 is shown including the geometric figure denoting the analyzer N 108N and its relative location. However, it should be recognized that the various embodiments and forms of the individual color overlays including changeable colors are applicable to, and can be used for, the other analyzers (e.g., analyzers 108A-108C) and the one or more pieces of ancillary test processing equipment 101 to denote an extent of a performance parameter and changes thereof.

Figure 3A:
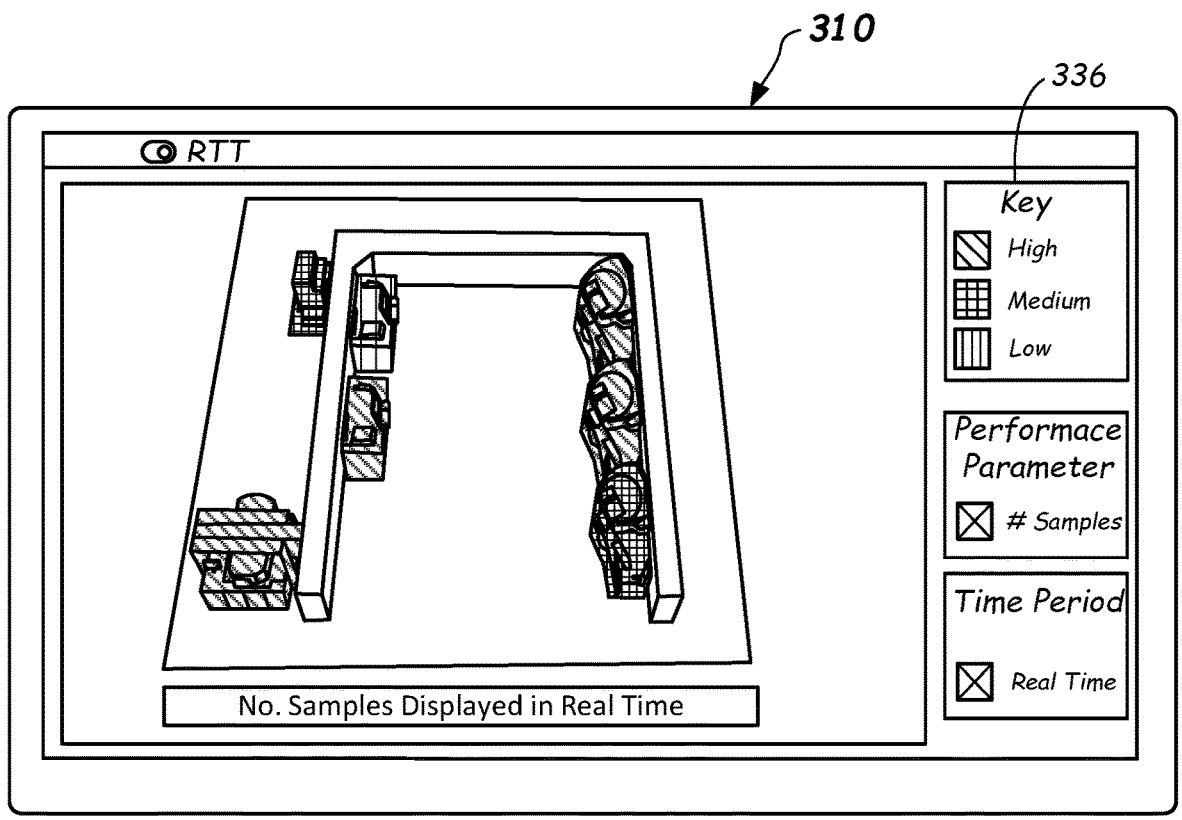
FIG. 3A illustrates a schematic diagram of a display that is displaying a three-dimensional (3D) image of the layout of the laboratory analyzers and ancillary test processing equipment together with a dynamically-changeable color overlay, according to one or more embodiments.
Figure 3B:
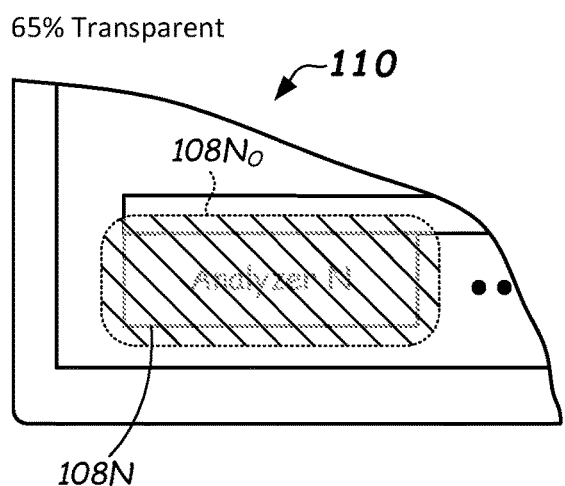
FIG. 3B through 3I illustrate schematic diagrams of a portion of a display that is displaying a laboratory analyzer with different examples of individual colored overlays of the dynamically-changeable color overlay, according to one or more embodiments.

As shown, for example, FIG. 3B illustrates a color transparency (hatched to denote a green transparency—65% transparent as shown). The individual color overlay $108N_o$, is shown lying over and fully overlapping the image of the analyzer 108N. The dotted line is shown to denote the edge of the individual color overlay $108N_o$ for illustration purposes, and need not be included. The color of the individual color overlays described herein (e.g., individual color overlay $108N_o$ and others) may be changeable to other colors to denote a change of relative value of a performance parameter of the associated analyzer 108A-108N or piece of ancillary test processing equipment 101.

Figure 3C:
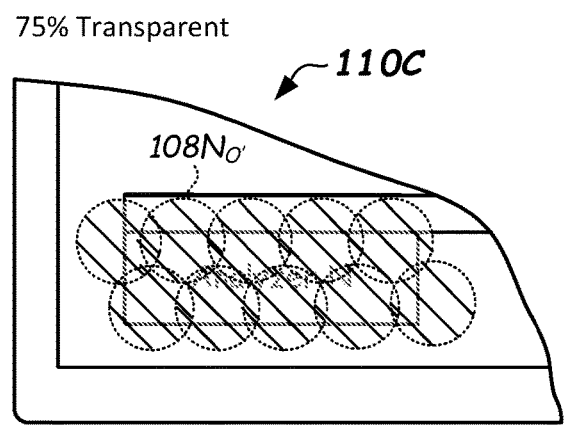

FIG. 3C illustrates a color transparency (hatched to denote a green transparency). The individual color overlay $108N_o$, is made up of a plurality of circles overlying portions of the geometric figure denoting the analyzer N 108N and its location. Collectively, the circles can fully overlap the image of the analyzer 108N, as shown, or may only partially overlap in some embodiments. The circles may optionally include some level of transparency (75% transparent as shown), as shown. The color of the individual color overlay $108N_o$ may be changeable to other colors (e.g., yellow, red, etc.) to denote a change in a value of a performance parameter.

Figure 3D:
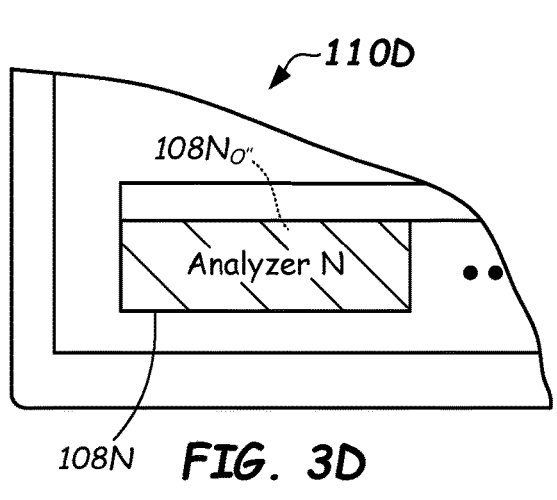

FIG. 3D illustrates an individual color overlay $108N_o"$ that comprises a solid color fill (e.g., hatched as green) that may completely fill within the border of the geometric figure denoting the analyzer N 108N and its location. Optionally, less than all of the confines within the perimeter border of the image of the analyzer 108N may be color filled to denote an extent of a performance parameter. Although shown solidly filled, the individual color overlay $108N_o"$ can include some level of transparency.

Figure 3E:
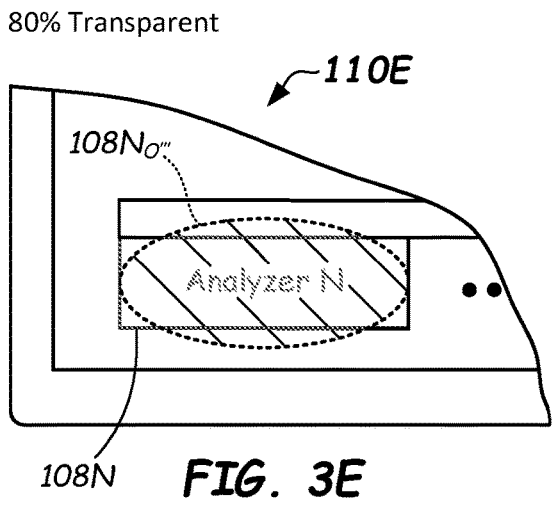

FIG. 3E illustrates an individual color overlay $108N_o'''$ that comprises a color fill (e.g., hatched as green) that may partially overlap the area of the geometric figure denoting the analyzer N 108N. The individual color overlay $108N_o'''$ can include some level of transparency (80% transparent as shown).

Figure 3F:
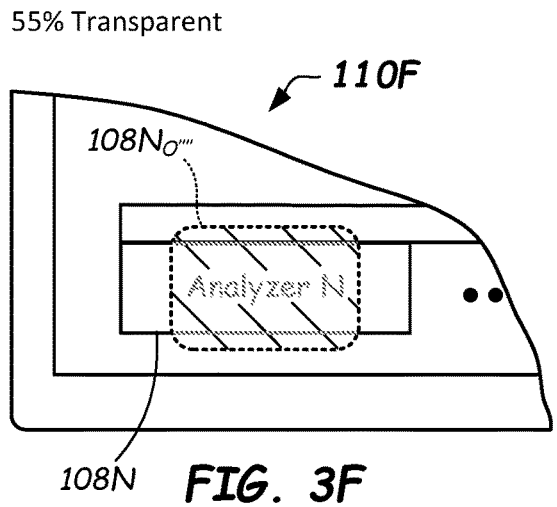

FIG. 3F illustrates an individual color overlay $108N_o''''$ that comprises a color fill (e.g., hatched as green) that may partially overlap the area of the geometric figure denoting the analyzer N 108N. The overlap may overlay less than 75% of the area of the geometric figure denoting the location of analyzer N 108N, for example. The individual color overlay $108N_o''''$ can include some level of transparency (55% transparent as shown).

Figure 3G:
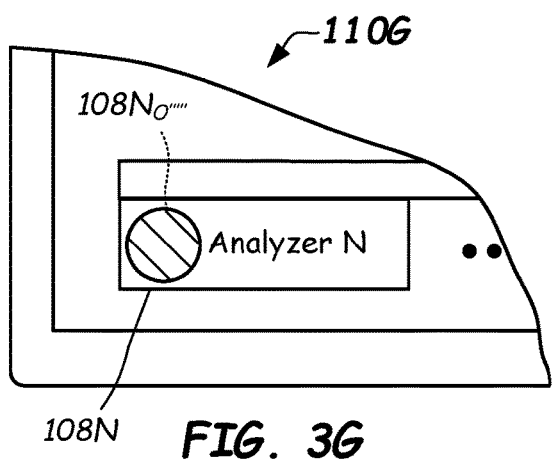

FIG. 3G illustrates an individual color overlay $108N_o''''$ that comprises a color fill (e.g., hatched as green) that may only partially overlap the area of the geometric figure denoting the analyzer N 108N. The overlap may overlie less than 50%, or even less than 25%, of the area of the geometric figure denoting the analyzer N 108N, for example. The individual color overlay $108N_o''''$ can be solidly filled or may include some level of transparency if desired.

Figure 3H:
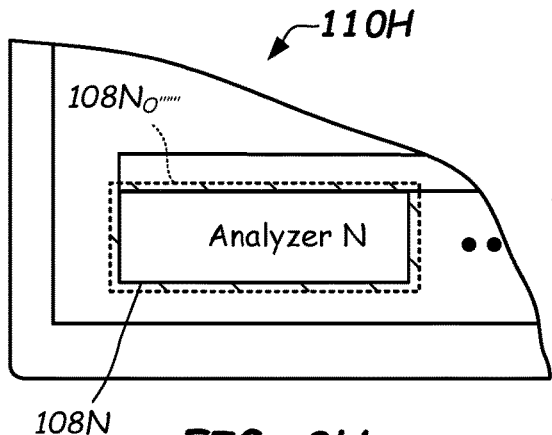

FIG. 3H illustrates an individual color overlay $108N_o'''''$ that comprises a color fill (e.g., hatched as green) that may surround the area of the geometric figure denoting the analyzer N 108N. The overlay may surround some or all of the area of the geometric figure denoting the analyzer N 108N, for example. The individual color overlay $108N_o'''''$ can be solidly filled (as shown) or may include some level of transparency. The individual color overlay $108N_o'''''$ may be round, oval, rectangular, square, hexagonal, or the like. Any desired polygonal shape may be used.

Figure 3I:
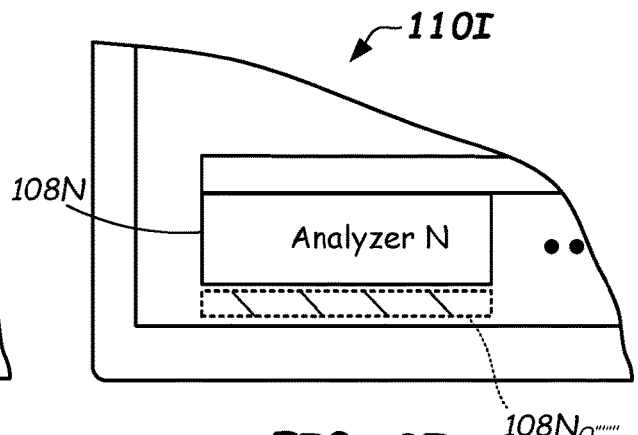

FIG. 3I illustrates an individual color overlay $108N_o''''''$ that comprises a color fill (e.g., hatched as green) that may be immediately proximate the area of the geometric figure denoting the analyzer N 108N. The overlay may be close enough to the location so that the individual color overlay $108N_o''''''$ is unmistakably associated with the particular analyzer N 108N, such as within an inch or two from an edge of the geometric figure, for example. The individual color overlay $108N_o''''''$ can be solidly filled (as shown) or may include some level of transparency.

The plurality of individual color overlays (e.g., color overlays $108A_o$-108NO, $122_o$, $124_o$, $126_o$, $128_o$, $130_o$) may, in some embodiments, include a suitable level of transparency such that the representative geometric figures and possible a label or name of the laboratory analyzer 108A-108N (and optionally also the pieces of ancillary test processing equipment 101 if desired) can be seen through the colored transparency.

Thus, as should be apparent, many forms of the individual color overlay are possible, such as solid or transparent, fully overlapping or partially overlapping, fully filling or partially filling, fully or partially surrounding, or immediately proximate.

As should be apparent from the above examples, each of the plurality of individual color overlays (e.g., $108N_o$, $108N_{o'}$, etc.) is color changeable between a plurality of colors. For example, the color of each of the plurality of individual color overlays (e.g., $108N_o$, $108N_{o'}$, etc.) can be changeable individually between two or more colors, three or more colors, four or more colors, or even five or more colors. Overlaying the representative geometric figures in the image 112 with individual color overlays of the dynamically-changeable color overlay 134 is used to indicate a particular performance for the plurality of laboratory analyzers 108A-108N (and optionally also the pieces of ancillary test processing equipment 101 if desired) over a period of time. The period of time can be in real time (instantaneous), a running average, or over any pre-selected or user-selectable period of time. The selected period of time may be preset in some embodiments. Any measurable or countable performance parameter can be displayed. The performance parameter can be selectable by a user/viewer (user selectable) in some embodiments. For example, as shown in FIG. 3J, the performance parameter to be displayed as a dynamically-changeable color overlay 134 can be selected by a user in a drop down menu 335. Optionally, a preset number of performance parameters may be displayed on separate display screens. In some embodiments, as user selectable menu may be provided for the pieces of ancillary test processing equipment 101, which may be a separate drop down menu for the plurality of laboratory analyzers 108A-108N. The period of time to display can be user selectable as well, such as is shown in FIG. 3K.

In one example, the displayed colors for the dynamically-changeable color overlay may comprise a heat map colorization scheme. For example, the individual color overlays (e.g., $108N_o$, $108N_{o'}$, etc.) can be changeable between at least the colors green, yellow, and red. Green can signify a high level of the selected performance parameter, yellow can signify an intermediate or medium level of the selected performance parameter, and red can signify a low level of the selected performance parameter. For example, when the selected performance parameter is throughput, i.e., the number of tests per the period of time for a particular analyzer (108A-108N), a high level of throughput would be colored green, yellow would signify an intermediate or medium level of throughput, and red would signify a low level of throughput for a particular analyzer 108A-0108N. Thus, at a glance, the user/viewer can readily understand the operation in regards to any selected performance parameter of individual ones of the analyzers 108A-108N, as well as the relative performance of the analyzers 108A-108N relative to other ones of the analyzers 108A-108N. Likewise, the user/viewer can readily understand the operation in regards to any selected performance parameter of individual ones of the pieces of ancillary test processing equipment 101, as well as the relative performance of the pieces of ancillary test processing equipment 101 relative to other ones of the pieces of ancillary test processing equipment 101. These color indicators can enable the user to ready understand how any change has affected the performance of the laboratory analyzer system 100. It may also allow the user to effectuate further changes to aid in balancing load between applicable analyzers 108A-108N and even between pieces of ancillary test processing equipment 101.

As shown in FIGS. 1 and 3A, the display 110, 310 may include a key 136, 336, which identifies the significance of each of the colors applied to the individual color overlays (e.g., $108N_o$, $108N_{o'}$, etc.). For example, the key 136, 336 may include a plurality of color-coded boxes, as shown, wherein each box may include an identifier (e.g., High, Intermediate (or Medium), Low) illustrating the relevance of the particular color of each box. As shown, the key 136, 336 may denote a heat map colorization scheme, including at least green, yellow and red. Other suitable forms and numbers of colors of the key 136, 336 may be used. The key 136, 336 may include more gradations than three, such as four, or five, or more.

Figure 4:
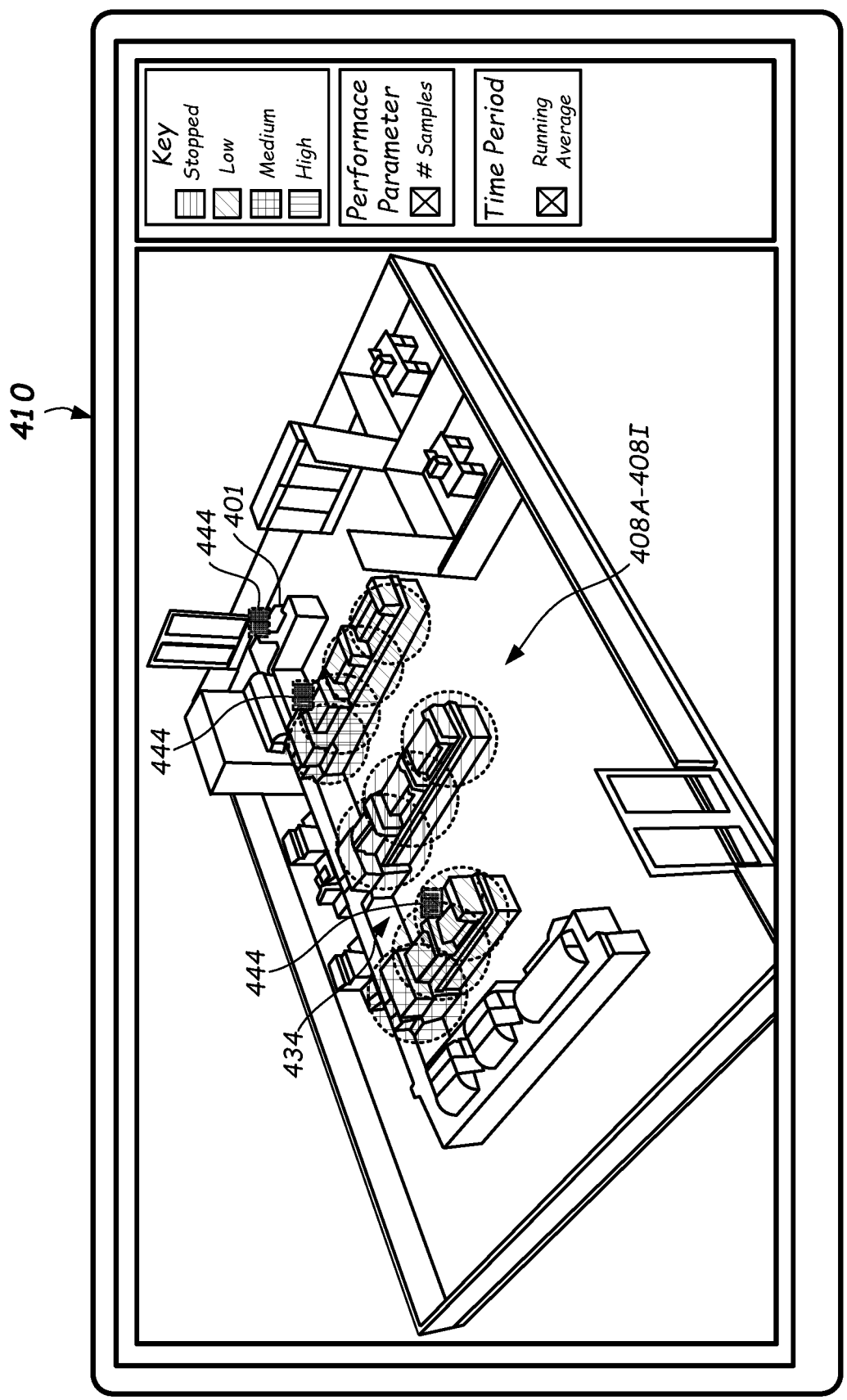
FIG. 4 illustrates screen shot of a display that is shown displaying a three-dimensional (3D) image of the layout of the laboratory analyzers and ancillary test processing equipment together with a dynamically-changeable color overlay, according to one or more embodiments.

In some embodiments, such as shown in FIG. 3L, the gradations may include numerical counts, such as 1-100, 101-200, 201-300, wherein a color may be associated with each count range. This may be used to indicate levels inventory wherein 1-100 may be denoted as red signifying near empty, 101-200 may be yellow meaning about half full, and 201-300 may be green meaning full or near full. Thus the user/viewer can readily see which ones of the analyzers 108A-108N need restocking with an inventory item. A specific key may be displayed that is applicable for each particular performance parameter. In some embodiments, such as shown in FIG. 4, more than one dynamically-changeable color overlay may be shown overlying a particular analyzer or piece of ancillary process equipment. For example, dynamically-changeable color overlay can indicate a performance parameter and another can indicate an inventory level. They each can be displayed simultaneously, giving the user an immediate indication of the selected performance in terms of the selected performance parameter and inventory remaining.

Thus, as should be understood, in one aspect, the present disclosure discloses a diagnostic laboratory system 100. The diagnostic laboratory system 100 comprises a lab server 102 having a processor 104 and memory 106, and a plurality of laboratory analyzers 108A-108N configured to communicate with the lab server 102, wherein each of the plurality of laboratory analyzers further configured to perform tests on biological samples. The lab server 102 further comprises a display 110 configured to display an image 112 representing a layout of a plurality of laboratory analyzers 108A-108N, a performance database 114 stored in the memory 106 configured to receive performance data 116 regarding the plurality of laboratory analyzers 108A-108N; and a color overlay module 118 comprising computer executable instructions configured to generate a dynamically-changeable color overlay to be displayed relative to the layout whose colors are changeable based on the performance data 116 received in the performance database 116 regarding the plurality of laboratory analyzers 108A-108N. The individual dynamically-changeable color overlays (e.g., $122_o$, $124_o$, $126_o$, $128_o$, $130_o$, and $108AO\text{-}108N_o$) can be provided graphically as separate layers overlying the image, for example. The individual dynamically-changeable color overlays can be made by any suitable modeling software and colored and/or shaded or filled by any suitable graphic shader as part of 2D or 3D scene; or as a 2D filled, shaded, or radial gradient-filled polygonal figure (e.g., square, rectangle, circle, oval, ellipse, or overlapping ones of the afore-mentioned) set to always face the virtual camera in a 3D scene. An algorithm may be used to select the color of the individual dynamically-changeable color overlays based upon the selected performance data over selected or preset period of time. Other suitable methods for shading, filling, or overlaying the image with color changes may be used.

FIG. 4 illustrates another embodiment of a display 410 displaying an image of a three-dimensional (3D) layout of analyzers 408A-408I. The layout is overlaid or otherwise shaded with a dynamically-changeable color overlay 434. The dynamically-changeable color overlay 434 can include individual color overlays (each shown with a dotted border) whose colors are dynamically changeable over time to express a level of a selected performance parameter. As shown, overlying each applicable image of an analyzer 408A-408I is a fuzzy-colored circular haze or colored transparency (with dotted circle outlines shown for illustration purposes) that is changeable in color, such as between blue, green, yellow, and red. The haze can be uniform in color or have a gradient, such as more having a more intense color (e.g., more color) at the center. Each color denotes a certain level or extent of a performance parameter. As shown, the performance parameter is number of samples per unit time, which can be a running average. Other performance parameters could be selected. Other colors could be use as well as other forms and shapes of the dynamically-changeable individual color overlays. The meaning of the colors may be user defined or optionally pre-defined in software.

Also shown are individual colored overlays 444 shown directly proximate to the location of at least some of the particular analyzers 408A-408N or pieces of ancillary test processing equipment 401. These individual overlays 444 can be used to express a level of an inventory item. For example, an individual overlays 444 can be colored green when an adequate supply of the inventory item is present, yellow when the supply is waning, and red when nearly out or in need of attention. Like individual colored overlays of changeable colors could be used to identify status of waste items, such as waste liquids or waste bins being full and in need of emptying (e.g., red), being near full (yellow), or being empty or near empty (e.g., green).

Figure 5:
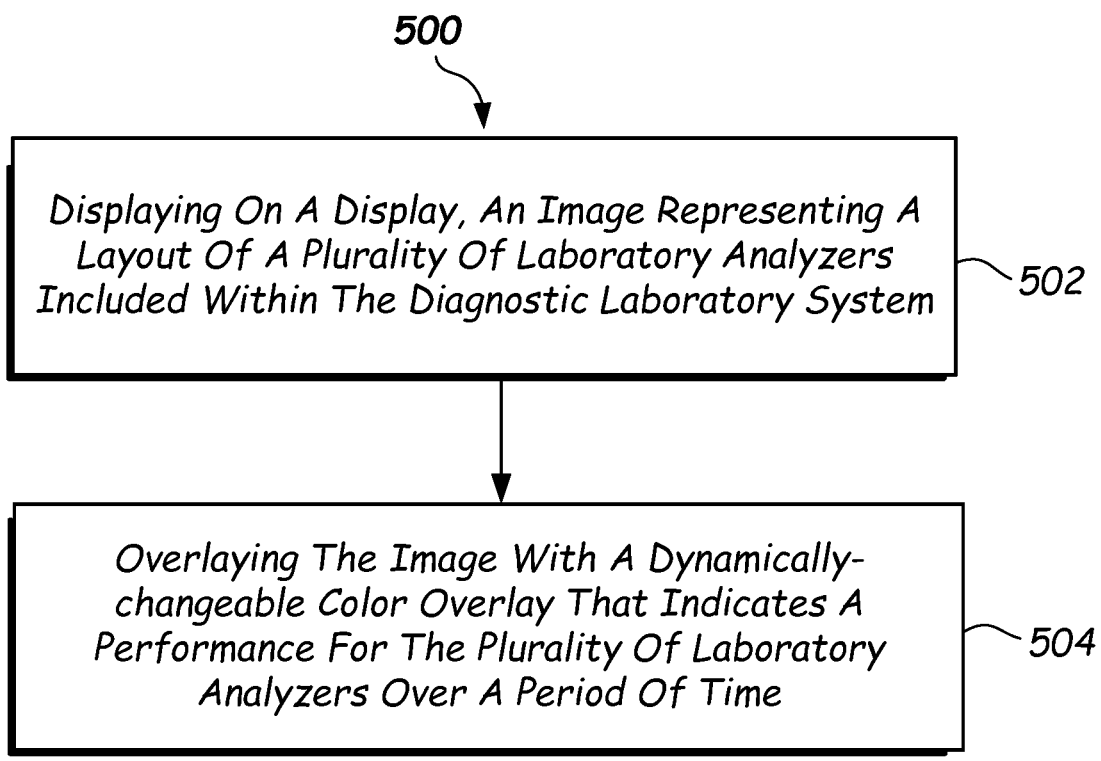
FIG. 5 illustrates a flowchart of a method of visualizing performance of a diagnostic laboratory according to one or more embodiments.

FIG. 5 illustrates a flowchart of a method 500 of visualizing performance of a diagnostic laboratory system (e.g., diagnostic laboratory system 100) according to one or more embodiments of the disclosure. Method 500 may be carried out by any suitable server, such as lab server 102. Method 500 may include, at process block 502, displaying on a display (e.g., display 110), an image (e.g., image 112) representing a layout of a plurality of laboratory analyzers (e.g., plurality of laboratory analyzers 108A-108N) included within the diagnostic laboratory system (e.g., diagnostic laboratory system 100). The image representing the layout may be a 2D image (see FIGS. 2A-2B) or 3D image (See FIGS. 3A and 4). The image 112 of the layout may be displayed as pixels on a suitable display screen or optionally as a projected image on a projection surface, for example. Other means for displaying the image may be used. The image may be generated using any suitable modeling software. Any suitable mechanism for display can be used.

The displayed image 112 may include any combination of geometric figures representative of the layout of the plurality of laboratory analyzers 108A-108N in the diagnostic laboratory system. For example, as best shown in FIG. 2B, the image 112 of the layout has the plurality of laboratory analyzers 108A-108N depicted as simple rectangular geometric polygonal blocks provided about another polygonal geometrical figure representing an automated track 120, wherein the plurality of laboratory analyzers 108A-108N are provided at approximate locations of the actual analyzers so that the user/viewer can make a quick spatial reference thereto. Also included in the image 112, as shown, may be geometric polygonal figures representing a layout of a plurality of ancillary test processing apparatus 101 that are ancillary to the plurality of laboratory analyzers 108A-108N. Ancillary test processing apparatus 101 are devices that perform one or more processes on the sample or the sample container prior to be send to an analyzer 108A-108N for analysis (i.e., pre-processing). Examples of the plurality of ancillary test processing apparatus 101 are loader 122, desealer 124, centrifuges 128, 130, and decapper 126. Other and/or different ancillary test processing apparatus 101 may be included in the image 112.

Method 500 may also include, in process block 504, overlaying the image (e.g., image 112) with a dynamically-changeable color overlay (e.g., dynamically-changeable color overlay 134) that indicates a performance for the plurality of laboratory analyzers (e.g., plurality of laboratory analyzers 108A-108N) over a period of time. The dynamically-changeable color overlay (e.g., dynamically-changeable color overlay 134) can also indicate a performance of the plurality of ancillary test processing apparatus (e.g., plurality of ancillary test processing apparatus 101) that are ancillary to the plurality of laboratory analyzers (108A-108N).

As best shown in FIG. 2C, the dynamically-changeable color overlay (e.g., dynamically-changeable color overlay 134) can be made up of individual color overlays, such as individual color overlays $122_o$, $124_o$, $126_o$, $128_o$, $130_o$, and $108A_o$, $108B_o$, $108B_o$, . . . , and $108N_o$. There may be an individual color overlay per each of the plurality of laboratory analyzers 108A-108N, and optionally also per each of the plurality of ancillary test processing apparatus 101. Each of the individual color overlays can include a dynamically-changeable color that is changeable in response to a change of performance data 116 received in the performance database over a period of time. The period of time may be in real time, a running average, or over any selectable or preselected period of time.

Thus, each of the individual color overlays associated with a particular analyzer 108A-108N can include a dynamically-changeable color that changes as the performance (e.g., a selected performance parameter) of the particular analyzer 108A-108N changes. Likewise, each of the individual color overlays associated with a particular piece of ancillary test processing apparatus 101 can include a dynamically-changeable color that changes as the performance of the particular piece of ancillary test processing apparatus 101 changes. Thus, over any particular period of time, a running time average, or in real time, the user/view can readily see and visualize the performance of a particular selected performance parameter in real time, as a running average over time, or over a selected period of time. For example, the selected parameter may be selected by the user/viewer from a drop-down menu as shown in FIG. 3I. The performance data may be received directly from the particular analyzer 108A-108N and/or particular piece of ancillary test processing apparatus 101 in some embodiments. Optionally, the data may be received from another program, such as from a middle ware program 117 that collects certain performance data, such as data regarding inventory levels of inventory items resident at various analyzers 108A-108N or particular pieces of ancillary test processing apparatus 101.

In another embodiment, a non-transitory computer readable storage medium is provided. The non-transitory computer readable storage medium refers to computer-readable media (CRM) that stores data for short periods or in the presence of power such as a memory device or Random Access Memory (RAM). Non-transitory computer readable storage medium further comprises a color overlay module 118 having computer-executable instructions (software instructions) that, when executed by the processor 104, cause the processor 104 of the lab server 102 to perform functions of receiving, storing, generating, and causing display. In particular, the computer-executable instructions enable the receiving of performance data 116 in the performance database 114 for the diagnostic laboratory system 100 comprising a plurality of laboratory analyzers 108A-108N. The receiving of performance data 116 in the performance database 114 can be enabled by a TCP/UDP socket communication of device-dependent protocols or the like.

Further, the computer-executable instructions enable the storage of the performance data 116 in a performance database 114. Performance data 116 can be data on any of the performance parameters discussed herein. The performance data 116 is stored in the performance database 114 by storage procedures, database writes, or other typical techniques used to store data in a database. Additionally, the computer-executable instructions enable the generation of image data of an image 112 of a layout (the spatial payout) of the plurality of laboratory analyzers 108A-108N. The image data is generated by comparing the current performance parameter against a baseline or threshold (single value or range) for that parameter for that laboratory analyzer 108A-108N and/or particular piece of ancillary test processing apparatus 101 and thereby deriving a color indicative of that level of performance and is rendered as a dynamically-changeable color overlay 134 for the particular laboratory analyzer 108A-108N and/or particular piece of ancillary test processing apparatus 101 on the display 110.

Also, the computer-executable instructions enable the generation of the dynamically-changeable color overlay 134. The dynamically-changeable color overlay 134 is generated in software by a graphics generator including a shader with pixel addressability. The colors assigned to each of the plurality of laboratory analyzers 108A-108N are generated based on the preselected or user selected performance parameter and the preset or selectable period of time. Faceted or linear shading may be used. Optionally ray tracing or Phong shading may be used. Testing the performance data against threshold rules can designate the color to be displayed based on the performance data for the particular performance parameter to be displayed. For example, a color corresponding to a particular numerical count can be displayed based on falling within a threshold range. There may be a particular threshold range for each color, wherein if the value of the performance parameter falls within a specified range, a certain color is to be displayed.

Finally, the computer-executable instructions cause the display of the dynamically-changeable color overlay 134 relative to image 112 of the layout of the plurality of laboratory analyzers 108A-108N based on the performance data 116, wherein respective colors of the dynamically-changeable color overlay are changeable in response to a change in a performance parameter. The computer-executable instructions generate a scene file that is displayed as of the dynamically-changeable color overlay 134 on the display 110. A scene file contains geometry, viewpoint, texture, lighting, and shading information as a description of the virtual scene.

While the disclosure is susceptible to various modifications and alternative forms, specific method and apparatus embodiments have been shown by way of example in the drawings and are described in detail herein. It should be understood, however, that the particular methods and apparatus disclosed herein are not intended to limit the disclosure but, to the contrary, to cover all modifications, equivalents, and alternatives falling within the scope of the claims.

The invention claimed is:

1. A diagnostic laboratory system, comprising:
   a lab server having a processor and memory; and
   a plurality of laboratory analyzers configured to communicate with the lab server, each of the plurality of laboratory analyzers further configured to perform tests on biological samples; and
   the lab server further comprising:
      a display configured to display an image representing a layout of a plurality of laboratory analyzers;
      a performance database stored in the memory configured to receive performance data regarding the plurality of laboratory analyzers; and
      a color overlay module comprising computer executable instructions configured to generate a dynamically-changeable color overlay to be displayed relative to the layout whose colors are changeable based on the performance data received in the performance database regarding the plurality of laboratory analyzers.

2. The diagnostic laboratory system of claim 1, wherein the dynamically-changeable color overlay further comprises individual colored overlays corresponding to each of the plurality of laboratory analyzers.

3. The diagnostic laboratory system of claim 1, wherein the dynamically-changeable color overlay further comprises individual color overlays corresponding to a plurality of ancillary test processing apparatus that are ancillary to the plurality of laboratory analyzers.

4. A non-transitory computer readable storage medium, comprising:
   a color overlay module having computer executable instructions configured to cause a lab server to:
   receive performance data for a diagnostic laboratory system comprising a plurality of laboratory analyzers;
   store the performance data in a performance database;
   generate image data of an image of a layout of the plurality of laboratory analyzers;
   generate a dynamically-changeable color overlay; and
   cause the display of the dynamically-changeable color overlay relative to image of the layout of the plurality of laboratory analyzers based on the performance data, wherein respective colors of the dynamically-changeable color overlay are changeable in response to a change in performance.

* * * * *